United States Patent
Amos et al.

(10) Patent No.: US 9,351,665 B2
(45) Date of Patent: May 31, 2016

(54) METHOD AND SYSTEM FOR DETECTING A RESPIRATORY SIGNAL

(75) Inventors: Yariv Avraham Amos, Hadera (IL); Gil Kaminski, Givat Shmuel (IL); Deganit Barak-Shinar, RaAnana (IL)

(73) Assignee: Widemed Technologies Ltd., Herzlia (IL)

( * ) Notice: Subject to any disclaimer, the term of this patent is extended or adjusted under 35 U.S.C. 154(b) by 508 days.

(21) Appl. No.: 13/144,502

(22) PCT Filed: Jan. 14, 2010

(86) PCT No.: PCT/IL2010/000039
§ 371 (c)(1),
(2), (4) Date: Jul. 14, 2011

(87) PCT Pub. No.: WO2010/082200
PCT Pub. Date: Jul. 22, 2010

(65) Prior Publication Data
US 2011/0275910 A1    Nov. 10, 2011

Related U.S. Application Data

(60) Provisional application No. 61/144,483, filed on Jan. 14, 2009.

(51) Int. Cl.
*A61B 5/08* (2006.01)
*A61B 5/024* (2006.01)
*A61B 5/1455* (2006.01)

(52) U.S. Cl.
CPC ........... *A61B 5/0816* (2013.01); *A61B 5/02416* (2013.01); *A61B 5/1455* (2013.01)

(58) Field of Classification Search
CPC combination set(s) only.
See application file for complete search history.

(56) References Cited

U.S. PATENT DOCUMENTS

| | | | |
|---|---|---|---|
| 4,815,473 | A | 3/1989 | Watson et al. |
| 5,083,560 | A | 1/1992 | Tillery, Jr. |
| 6,142,953 | A | 11/2000 | Burton et al. |
| 6,377,845 | B1 | 4/2002 | Kinast |
| 6,932,774 | B2 | 8/2005 | Nakatani et al. |
| 7,177,686 | B1 | 2/2007 | Turcott |
| 7,351,208 | B2 | 4/2008 | Brodnick et al. |

(Continued)

FOREIGN PATENT DOCUMENTS

| | | |
|---|---|---|
| WO | WO 00/21438 | 4/2000 |
| WO | WO 2006/082589 | 8/2006 |

(Continued)

OTHER PUBLICATIONS

Chua, C-P., et al. "Towards automated sleep state estimation using a Holter-oximeter." Engineering in Medicine and Biology Society, 2007. EMBS 2007. 29th Annual International Conference of the IEEE. IEEE, 2007 (Chua).* International Preliminary Report on Patentability Dated Jul. 28, 2011 From the International Bureau of WIPO Re. Application No. PCT/IL2010/000039.

(Continued)

*Primary Examiner* — Michael Kahelin
*Assistant Examiner* — Mitchell E Alter

(57) ABSTRACT

A method of analyzing a plethysmograph signal is disclosed. The method comprises: extracting from the signal a plurality of features, thereby constructing a feature space. The method further comprises employing a path selection procedure to the feature space for determining at least one sequence of respiration frequencies and reconstructing a respiratory signal using the sequence.

20 Claims, 3 Drawing Sheets
(1 of 3 Drawing Sheet(s) Filed in Color)

(56) References Cited

U.S. PATENT DOCUMENTS

| | | |
|---|---|---|
| 7,801,591 B1 * | 9/2010 | Shusterman .................. 600/509 |
| 2003/0163054 A1 | 8/2003 | Dekker |
| 2004/0230105 A1 * | 11/2004 | Geva et al. .................... 600/301 |
| 2006/0064037 A1 * | 3/2006 | Shalon et al. ................. 600/586 |
| 2006/0195037 A1 | 8/2006 | Wiesel |
| 2006/0258921 A1 * | 11/2006 | Addison et al. ............... 600/323 |
| 2007/0213620 A1 | 9/2007 | Reisfeld |
| 2007/0213621 A1 | 9/2007 | Reisfeld et al. |
| 2007/0213622 A1 | 9/2007 | Reisfeld |
| 2007/0213624 A1 | 9/2007 | Reisfeld et al. |
| 2008/0167564 A1 | 7/2008 | Hete et al. |
| 2008/0269583 A1 | 10/2008 | Reisfeld |

FOREIGN PATENT DOCUMENTS

| | | |
|---|---|---|
| WO | WO 2009/118737 | 10/2009 |
| WO | WO 2010/082200 | 7/2010 |

OTHER PUBLICATIONS

International Search Report and the Written Opinion Dated May 17, 2010 From the International Searching Authority Re.: Application No. PCT/IL2010/000039.

Ricke et al. "Automatic Segmentation of Heart Sound Signals Using Hidden Markov Models", Computers in Cardiology, XP002580358, 32: 953-956, 2005.

* cited by examiner

METHOD AND SYSTEM FOR DETECTING A RESPIRATORY SIGNAL

RELATED APPLICATIONS

This application is a National Phase of PCT Patent Application No. PCT/IL2010/000039 having International filing date of Jan. 14, 2010, which claims the benefit of priority of U.S. Provisional Patent Application No. 61/144,483 filed on Jan. 14, 2009. The contents of the above applications are all incorporated herein by reference.

FIELD AND BACKGROUND OF THE INVENTION

The present invention, in some embodiments thereof, relates to the detection of a respiratory signal and, more particularly, but not exclusively, to the detection of a respiratory signal by analysis of a plethysmograph signal, e.g., a photoplethysmograph signal.

An individual's health and fitness level may be determined by measuring his or her breathing patterns during respiration. In turn, respiration patterns also influence the fitness level and health of the individual. Two components of the measured respiration patterns are respiration rate and respiration depth. Respiration rate is a measure of the number of breaths taken per unit time, typically measured in breaths per minute. Respiration depth is a measure of the extent to which an individual's lungs expand and contract.

The respiration of an individual or patient may be monitored for a variety of reasons. For example, knowledge about a patient's respiration may assist a physician in assessing the patient's stability during surgery and recovery after surgery. Another rapidly growing field in which information about an individual's respiration may be of value is the field of sleep therapy.

Known in the art are monitoring systems that monitor the respiration frequency of the patient, record the respiration curve and indicate respiration irregularities such as apnea. Various such monitoring systems have been heretofore suggested and/or utilized in a variety of settings, and have included devices utilizing impedance or inductance plethysmography, aural monitoring, EMG or ECG monitoring, strain gauges and the like (see, e.g., U.S. Pat. Nos. 4,815,473, 5,083,560, 6,142,953, 6,377,845, 7,177,686 and 7,351,208).

Photoplethysmographic systems are widely used for monitoring the oxygen status of blood. A photoplethysmograph system typically includes a sensor which is typically attached to an adult patient's finger or an infant patient's foot. The sensor typically includes red and infrared (IR) light-emitting diodes (LEDs) and a photodiode detector. Light emitted from the LEDs passes through the tissue (finger or foot). The photodiode is positioned opposite to the LEDs so as to detect the light as it emerges from the tissue. Oxygen saturation is determined by computing the differential absorption by arterial blood of the two wavelengths emitted by the sensor.

Other than pure oximetry, the photoplethysmograph signal has been used for sleep monitoring and diagnosis of periodic breathing including detection of sleep apnea events, detection of cardiac arrhythmias and heart failure and prognosis of heart disease (see, e.g., International Patent Publication No. WO2009/118737, and U.S. Published Application Nos. 20070213620, 20070213621, 20070213622 and 20070213624, the contents of which are hereby incorporated by reference).

SUMMARY OF THE INVENTION

According to an aspect of some embodiments of the present invention there is provided a method of analyzing a plethysmograph signal. The method comprises: extracting from the signal a plurality of features, thereby constructing a feature space; employing a path selection procedure to the feature space for determining at least one sequence of respiration frequencies; reconstructing a respiratory signal using the sequence; and transmitting the respiratory signal to a computer readable medium.

According to some embodiments of the invention the method comprises using the sequence of respiration frequencies for selecting a corresponding sequence of respiration tidal volumes.

According to some embodiments of the invention method comprises analyzing the signal for detecting temporal segments corresponding to a physiological event, wherein the path selection procedure is employed separately for different types of physiological events.

According to some embodiments of the invention the method comprises updating the feature space following identification of a segment corresponding to a physiological event.

According to some embodiments of the invention the method comprises calculating a transfer function filter for each segment other than segments corresponding to physiological events, wherein the updating of the feature space comprises filtering a respective segment corresponding to a respective physiological event using a transfer function filter of a preceding segment.

According to an aspect of some embodiments of the present invention there is provided an apparatus for analyzing a plethysmograph signal. The apparatus comprises an input unit for receiving the plethysmograph signal; and a data processor configured for extracting from the signal a plurality of features thereby constructing a feature space; employing a path selection procedure to the feature space for determining at least one sequence of respiration frequencies; and reconstructing a respiratory signal using the sequence.

According to an aspect of some embodiments of the present invention there is provided a plethysmograph system, comprising: a plethysmograph sensor configured for generating a plethysmograph signal and an analysis apparatus, such as the apparatus delineated above and as further detailed hereinbelow.

According to some embodiments of the invention the data processor is configured for using the sequence of respiration frequencies for selecting a corresponding sequence of respiration tidal volumes.

According to some embodiments of the invention the data processor is configured for analyzing the spectral parameters for temporal segments corresponding to a physiological event, wherein the path selection procedure is employed separately for different types of physiological events.

According to some embodiments of the invention the data processor is configured for updating the feature space following identification of segment corresponding to a physiological event.

According to some embodiments of the invention the data processor is configured for calculating a transfer function filter for each segment other than segments corresponding to physiological events, wherein the updating of the feature space comprises filtering a respective segment corresponding to a respective physiological event using a transfer function filter of a preceding segment.

According to some embodiments of the invention the features are selected from the group consisting of respiration parameters, spectral parameters and signal envelope parameters.

According to some embodiments of the invention the physiological event is selected from the group consisting of atrial fibrillation, periodic limb movements and apnea.

According to some embodiments of the invention the path selection procedure comprises an expectation maximization algorithm.

According to some embodiments of the invention the plethysmograph signal is a photoplethysmograph signal.

According to some embodiments of the invention the path selection procedure features a hidden Markov model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram illustrating a method suitable for analyzing a plethysmograph signal of a subject, according to various exemplary embodiments of the present invention;

FIG. 2 shows a representative example of a spectrogram describing a photoplethysmograph spectrum for a subject with normal rhythm;

FIG. 3 is a schematic illustration of a discrete hidden Markov ergodic model, which can be employed according to some embodiments of the present invention;

FIG. 4 is a schematic illustration of an apparatus for analyzing a plethysmograph signal, according to various exemplary embodiments of the present invention; and FIG. 5 is a schematic illustration of a plethysmograph system, according to various exemplary embodiments of the present invention.

Figure 1:
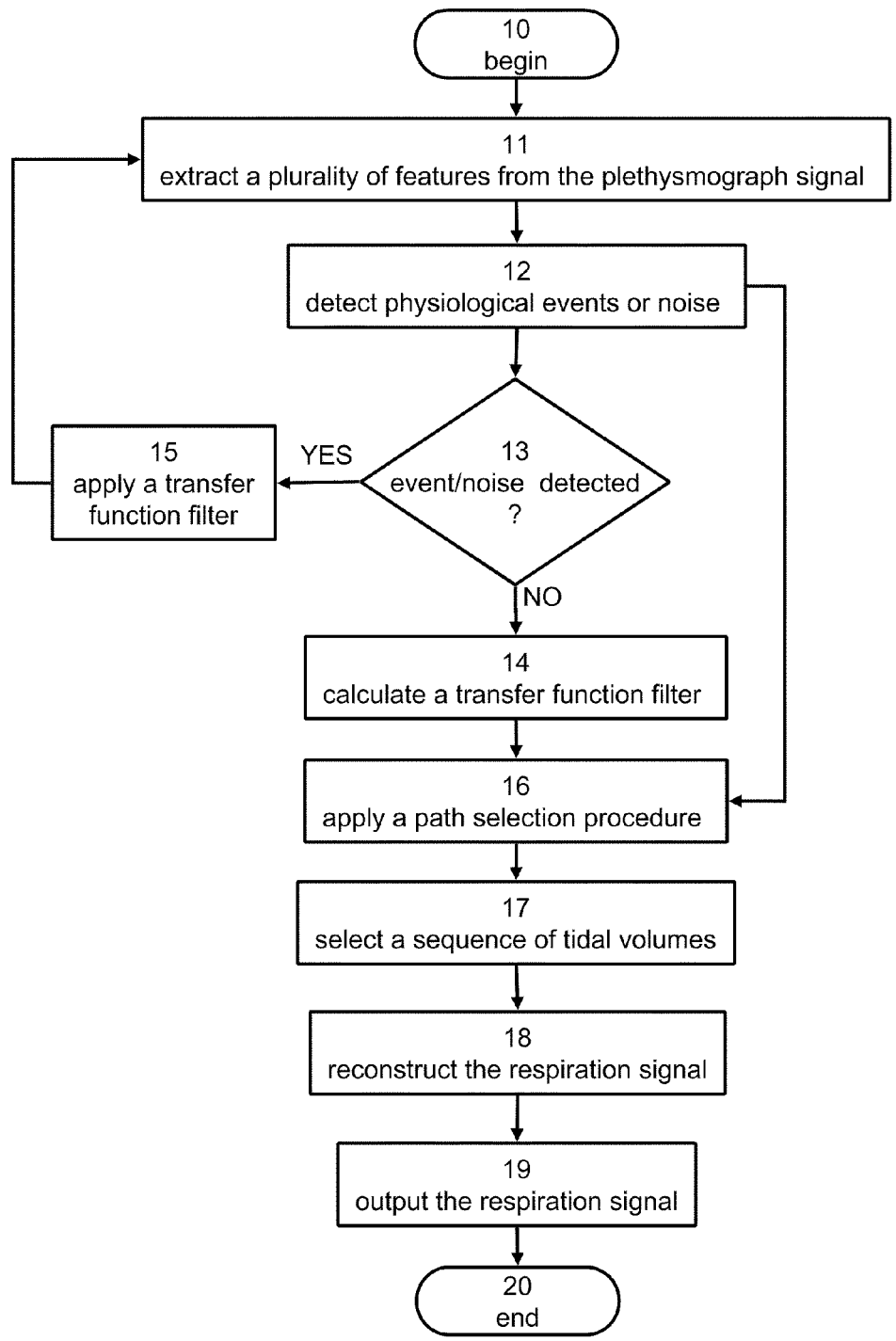

DESCRIPTION OF SPECIFIC EMBODIMENTS
OF THE INVENTION

The present invention, in some embodiments thereof, relates to the detection of a respiratory signal and, more particularly, but not exclusively, to the detection of a respiratory signal by analysis of a plethysmograph signal, e.g., a photoplethysmograph signal.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The plethysmograph signal contains components which are synchronous with heart pulses excited by the sinus node as well as with respiratory rhythm. The respiratory component of the signal is caused by respiratory synchronous blood volume variations. The present inventors devised a technique for analyzing a plethysmograph signal and, optionally and preferably, detecting a respiratory signal from the plethysmograph signal.

The detected respiratory signal can be transmitted to a computer readable medium, such as a hard drive or a computer memory, from which it is optionally and preferably read, e.g., for the purpose of displaying the signal and/or for further analysis. Once detected according to various exemplary embodiments of the present invention, the respiratory signal can be used for variety of medical purposes.

Congestive heart failure (CHF) patients, for example, suffer from respiratory discomfort or shortness of breath. Fluids accumulate in the interstitial tissues of the lungs of CHF patients due to high ventricular filling pressure. The CHF patient experiences respiratory dysfunction due to the lung congestion. A commonly observed symptom is shortness of breath which is aggravated when the CHF patient is lying in bed. The detected signal can be provided to the physician for optimizing therapy (e.g., pacing, drug therapy, auto-adjustment of positive airway pressure and servo-ventilator oxygen therapy) for the patient and optionally provide a prognosis.

The present embodiments are also useful in the field of sports medicine. Maximal athletic efforts are associated with muscular exhaustion as well as respiratory fatigue and exhaustion typically interpreted or perceived as uncontrolled exhaustive hyperventilation. Detection of a respiratory signal during exercise can aid a sports medicine physician diagnose a possible respiration disease and/or provide recommendation for appropriate training protocol.

The method, apparatus and system can be used directly within a hospital or other medical facilities. The apparatus and system can also be integrated into an electronic patient data acquisition system.

The method, apparatus and system of the present embodiments are also useful for monitoring the physical and medical condition of ambulatory patients, or independent or chronically ill persons. The present embodiments can also be utilized in work place medicine, since the respiratory signal can be detected while the subject is at work.

Some embodiments of the present invention can be implemented by a data processor, such as, but not limited to, a computer. Thus, some embodiments of the present invention can be embodied in on a tangible medium such as a computer for performing the method steps. It can be embodied on a computer readable medium, comprising computer readable instructions for carrying out the method described below. Some embodiments can be embodied in electronic device having digital computer capabilities arranged to run the computer program on the tangible medium or execute the instruction on a computer readable medium.

Computer programs implementing embodiments of this invention can commonly be distributed to users on a distribution medium such as, but not limited to, a floppy disk, CD-ROM a flash memory card or the like. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

Referring now to the drawings, FIG. 1 is a flowchart diagram illustrating a method suitable for analyzing a plethysmograph signal of a subject, according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagram is not to be considered as limiting. For example, two or more operations, appearing in the following description or in the flowchart diagram in a particular order, can be executed in a different order (e.g., a reverse order) or substantially contemporaneously. Additionally, several operations described below are optional and may not be executed.

The plethysmograph signal can be input to the method of the present embodiments from any plethysmograph system or device. Typically, such device includes a sensor, e.g., a pulse oximetry sensor which provides a photoplethysmograph signal indicative of blood flow and a signal indicative of the level of oxygen saturation in the patient's blood. Thus, in various exemplary embodiments of the invention the plethysmograph signal is a signal that is associated with blood oxygen saturation.

The method begins at 10 and continues to 11 at which a plurality of features is extracted from the signal. The features are preferably extracted segment-wise. In this embodiment, the signal is preferably segmented to a plurality of temporal segments, each corresponding to a different time window, and the features extraction is performed separately for each segment. The number of signal samples per segment is denoted $N_{sf}$. Representative examples of features suitable for the present embodiments include, without limitation, respiration parameters, spectral parameters and signal envelope parameters.

These features can be extracted using any procedure known in the art. For example, the following procedure can be used for extracting the respiration parameters. The signal is filtered using k band-pass filters. Typically, k equals 3. Following each such filtration, a peak detection and Fourier transform is employed to the baseline oscillations of the signal for calculating respiration parameters for the respective filter. The respiration parameters preferably include a set of candidate frequencies. More preferably, the respiration parameters preferably a set of tuples, each having a plurality of candidate frequencies. In other words, a peak detection procedure and Fourier transform is applied to the signal, preferably segment-wise, so as to detect one or more candidate frequency for each band-pass filter.

In various exemplary embodiments of the invention the method detects a pair candidate frequencies, for each band-pass filter, thereby providing a set of pairs denoted $\{f_{i1}, f_{i2}\}_{i=1}^{k}$. In some embodiments, the method also calculates a peak significance value for each pair of frequencies, thereby obtaining a set of respective peak significance values, denoted $\{p_i\}_{i=1}^{k}$. A peak significance value is interchangeably referred to hereinunder as "relative energy."

The peak significance value $p_i$ (i=1, ..., k) can be calculated directly from the spectrum $Y_i$ of the signal after filtering by the ith band pass filter:

$$p_i = \frac{U[h_{i1} - h_{-min}] + U[h_{i1} - h_{+min}]}{2h_{i1}} \quad (1)$$

where:

U is a unit step function, $h_{i1}$, $h_{+min}$ and $h_{-min}$ are spectral intensities, respectively defined as $h_{i1}=abs(Y_i(j2\pi f_{i1}))$, $h_{+min}=abs(Y_i(j2\pi f_+))$ and $h_{-min}=abs(Y_i(j2\pi f_-))$, and $f_+$ and $f_-$ are frequencies corresponding to minima of $Y_i$ in the frequency intervals $[f_{i1}, f_{i1}+\Delta f/2]$ and $[f_{i1}-\Delta f/2, f_{i1}]$, respectively, where $\Delta f$ is a frequency window parameter which can be predetermined. A typical value for $\Delta f$ is 0.1 Hz.

The above procedure allows extraction of a vector, referred to herein as a respiration vector f defined as $f=\{f_{i1}, f_{i2}, p_i\}_{i=1}^{k}$. The procedure is preferably executed segment-wise. In this embodiment, the extracted respiration vector is denoted $f_t$, where the subscript t denotes the t-th temporal segment from which the respiration vector is extracted.

Techniques for extracting the respiration parameters are also disclosed in Nilsson et al., "Monitoring of respiratory rate in postoperative care using a new photoplethysmographic technique," J. Clin. Monit. Comput. 16 309-15, 2000; and Nakajima et al., "Monitoring of Heart and Respiratory Rates by Photoplethysmography Using a Digital Filtering Technique," Med. Eng. Phys., vol. 18, pp. 365-372, 1996, the contents of which are hereby incorporated by reference.

The following procedure can be used for extracting the spectral parameters. A spectrogram of the plethysmograph signal is obtained, and various candidate frequencies are identified on the spectrogram. The identified candidate frequencies can include, frequency of respiration, $f_r$, frequency associated with the heart rate $f_{hr}$, and various combination such as, but not limited to, $f_{hr}+f_r$ and $f_{hr}-f_r$.

The candidate frequencies can be identified by applying a Fourier transform was applied to the corresponding spectrum. This procedure typically results in identification of one main peak, which in various exemplary embodiments of the invention is declared as a frequency $f_{hr}$ associated with the heart rate of the subject. Typically, there are also two satellite peaks near the main peak, which in principle can be at both sides of the main peak, namely at frequencies slightly below and slightly above $f_{hr}$. The distances (over the frequency axis) between $f_{hr}$ and its closest satellite peaks from below and from above are denoted $f_{r1}$ and $f_{r2}$, respectively (namely the closest satellite peaks from below is $f_{-r1}=f_{hr}-f_{r1}$, and the closest satellite peaks from above is $f_{+r2}=f_{hr}+f_{r2}$). In some embodiments of the invention the peaks at $f_{-r1}$ and $f_{+r2}$ are detected and identified by the method. In some embodiments, the method approximates $f_{r1}=f_{r2}$. In these embodiments $f_{+r2}$ is interchangeably denoted $f_{+r1}$.

At a frequency below the main peak, farther from $f_{-r1}$, there is an additional peak, which in various exemplary embodiments of the invention is detected and identified as a candidate respiratory frequency denoted $f_r$.

The candidate frequencies that are identified from the spectrogram can be used as the extracted features. It was found by the inventors of the present invention that it is useful to define the following candidate frequencies: $f_r$, $f_{hr}$, $f_{-r1}$ and $f_{+r2}$. Various combinations of the identified candidate frequencies can also be used as the extracted features.

Figure 2:
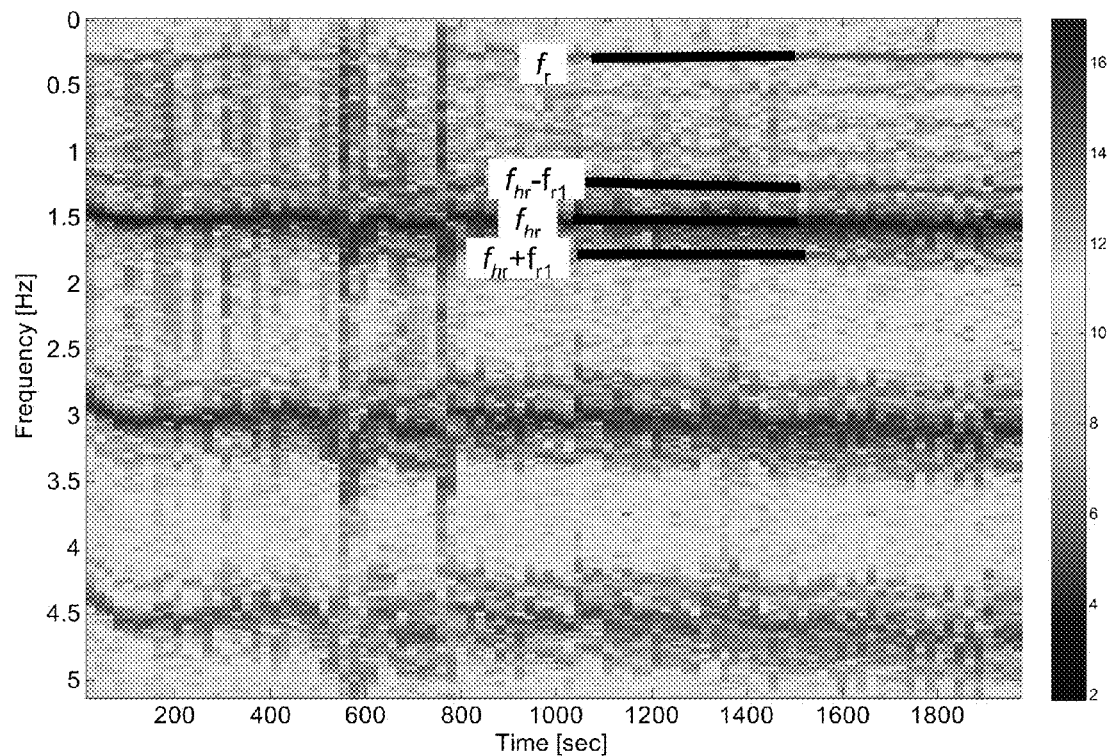

A representative example of such spectrogram is shown in FIG. 2. The color bar on the right hand side of FIG. 2 indicates the respective intensities in arbitrary energy units. The spectrogram describes photoplethysmograph spectrum for a subject with normal rhythm. Marked on FIG. 2 are four frequencies: $f_r$ which equals approximately 0.3 Hz, $f_{hr}-f_{r1}$ which equals approximately 1.2 Hz, $f_{hr}$ which equals approximately 1.5 Hz and $f_{hr}+f_r$ which equals approximately 1.8 Hz. Note that in this example, $f_{r1}$ and $f_{r2}$ are approximated to be the same and further that $f_r=f_{r1}=0.3$ Hz.

Optionally and preferably the method also calculates a peak significance value for one or more of the candidate frequencies and combination of frequencies. The peak significance value can be calculated using Equation 2 above by substituting $f_{i1}$ with the respective frequency. Thus, for example, in some embodiments of the present invention the method calculates the peak significance value of $f_r$, which peak significance value is referred to as $p_r$, in some embodiments the method calculates the peak significance value of $f_{-r1}$, which peak significance value is referred to as $p_{-r1}$, and in some embodiments the method calculates the peak significance value of $f_{+r1}$, which peak significance value is referred to as $p_{+r1}$.

The above procedure allows extraction of a vector, referred to herein as a spectral vector $\psi$, the components of which are the features extracted from the spectrogram. The procedure is preferably executed segment-wise. In this embodiment, the extracted spectral vector is denoted $\psi_t$, where the subscript t denotes the t-th temporal segment from which spectral vector is extracted. In various exemplary embodiments of the invention $\psi_t$ is defined as $\psi_t=[f_r, f_{-r1}, f_{-r1}, p_r, p_{-r1}, p_{-r1}]$. Other components for the vector $\psi$ are not excluded from the scope of the present invention. The extraction of the components of the vector $\psi$ is particularly useful in cases of slowly-varying respiration, slowly-varying heart rates and relatively high signal to noise ratios (SNR).

Techniques for extracting the spectral parameters are also disclosed in Clifton et al., "Measurement Of Respiratory Rate From The Photoplethysmogram In Chest Clinic Patients," Journal of Clinical Monitoring and Computing (2007) 21:55-61; Leonard et al., "A Fully Automated Algorithm For The Determination Of Respiratory Rate From The Photoplethysmogram," Journal of Clinical Monitoring and Computing (2006) 20: 33-36; and Shelley et al., "The Use Of Joint Time Frequency Analysis To Quantify The Effect Of Ventilation On The Pulse Oximeter Waveform," Journal of Clinical Monitoring and Computing (2006)20: 81-87, the contents of which are hereby incorporated by reference.

The signal envelope parameters typically include candidate frequencies corresponding to an upper and a lower envelope of the signal. These candidate frequencies are referred to herein as envelope frequencies and denoted $f_{+env}$ and $f_{-env}$, respectively. The frequencies can be calculated by identifying the upper and lower envelopes of the signal, interpolating the envelopes and extracting their fundamental frequencies. A representative example of such technique is disclosed in Nitzan et al., "Power Spectrum Analysis of Spontaneous Fluctuations in the Photoplethysmographic Signal," Journal of Basic & Clinical Physiology & Pharmacology, vol. 5, pp. 269-276, 1994, the contents of which are hereby incorporated by reference.

In some embodiments of the present invention the signal envelope parameters also include a fundamental frequency of the RR interval of the subject, which is known to be indicative of respiratory sinus arrhythmia (RSA). This frequency is referred to herein as candidate RSA frequency and denoted $f_{rsa}$. A representative example of a technique for extracting a fundamental frequency of an RR interval is disclosed in is disclosed in Ahlstrom et al., "A Respiration Monitor Based on Electrocardiographic and Photoplethysmographic Sensor Fusion," presented at 26th Annual International Conference of the IEEE EMBS, 2004; and Zhang et al., "Respiration Response Curve Analysis of Heart Rate Variability," *IEEE Transactions on Biomedical Engineering*, vol. 44, pp. 321-325, 1997, the contents of which are hereby incorporated by reference.

Optionally and preferably the method also calculates a peak significance value for one or more of the envelope and candidate RSA frequencies. The peak significance value can be calculated using Equation 2 above by substituting $f_{i1}$ with the respective frequency. Thus, for example, in some embodiments of the present invention the method calculates the peak significance value of $f_{+env}$, which peak significance value is referred to as $p_{+env}$, in some embodiments the method calculates the peak significance value of $f_{-env}$, which peak significance value is referred to as $p_{-env}$, and in some embodiments the method calculates the peak significance value of $f_{rsa}$, which peak significance value is referred to as $p_{rsa}$.

The above procedure allows extraction of a vector, referred to herein as an envelope vector $\eta$, the components of which are the envelope parameters. The procedure is preferably executed segment-wise. In this embodiment, the extracted envelope vector is denoted $\eta_t$, where the subscript t denotes the t-th temporal segment from which envelope vector is extracted. In various exemplary embodiments of the invention $\eta_t$ is defined as $\eta_t=[f_{+env}, f_{-env}, f_{+rsa}, p_{+env}, p_{-env}, p_{rsa}]$. Other components for the vector $\eta$ are not excluded from the scope of the present invention.

The extracted vectors, $f_t$, $\psi_t$ and $\eta_t$ span a multidimensional space referred to herein as the "feature space" of the t-th segment, denoted $o_t$. Thus, $o_t=[f_t, \psi_t, \eta_t]$. It is convenient to separate the feature space $o_t$ to a frequency part, $F_t$, and an energy part $E_t$. Frequency part $F_t$ includes all the candidate frequencies in $o_t$, e.g., at least some of $\{f_{i1},f_{i2}\}_{i=1}^{k}$, and $f_{+env}$, $f_{-env}$, $f_{+rsa}$, $f_r$, $f_{-r1}$ and $f_{+r1}$; and energy part E includes all the peak significance values in $o_t$, e.g., at least some of $\{p_i\}_{i=1}^{k}$, $p_{+env}$, $p_{-env}$, $p_{rsa}$, $p_r$, $p_{-r1}$ and $p_{-r1}$. Thus, $o_t$ can also be written as $o_t=[F_t, E_t]$.

At 12 the method optionally and preferably detects temporal segments which correspond to a physiological event. The physiological event generally indicates an abnormal rhythm. Optionally, the method identifies the type physiological event that is detected. Physiological events which can be detected include, but are not limited to apnea, cardiac events, such as atrial fibrillation (AFIB), tachycardia, premature ventricular contractions, bigemini and trigemini, and periodic limb movements (PLMs). Optionally and preferably at 12 the method also detects noise. For segments which are identified as noise with a level of confidence which is above a predetermined confidence level threshold (e.g., 90% or 95%), all candidate frequencies are preferably set to zero.

Abnormal physiological events can generally be identified as transient, non-stationary segments in the signal. Various methods may be used to detect the physiological events automatically. In some embodiments the signal is divided into quasi-stationary segments. For example, an adaptive segmentation procedure can be employed. In this embodiment the signal is divide into segments, each of which is characterized by quasi-stationary behavior.

The term "quasi-stationary" as used herein means that certain statistical properties of each segment, such as spectral amplitude variations, are contained within predefined bounds.

Segments that are not quasi-stationary over at least a predefined minimum duration may be identified as transient events, which may include abnormal physiological events. An adaptive segmentation procedure useful for the present embodiments are described in detail in the U.S. Published Application No. 20040230105, the contents of which are hereby incorporated by reference.

Upon identifying an abnormal physiological event, the respective segment and optionally one or more segments before and after the respective segment are collected in order to gather event statistics. The statistics gathered may include, for example, the duration of the event, the variance and frequency of changes in physiological parameters during and after the event, and the time required for recovery of these parameters to steady-state values after the event.

Detection of an apnea event can include, for example, processing the signal to detect patterns corresponding to multiple cycles of periodic breathing. In some embodiments of the present invention the signal filtered by a low-pass filter to remove signal components at frequencies that are greater than or equal to the patient's respiratory frequency, such that the remaining signal reflects trends over multiple respiratory cycles. In some embodiments, the filtering is even more pronounced, and eliminates frequency components outside the Cheyne-Stokes cycle frequency, for example, components below 1/180 Hz or above 1/40 Hz. In some embodiments of the present invention the periodic breathing pattern is classified according to an origin of the periodic breathing based on the symmetry of the pattern. The origin can be predominantly central, predominantly obstructive, or a mixture of central and obstructive.

Detection of atrial fibrillation or any other type of arrhythmia can be done by analyzing the signal (e.g., spectral analysis) to identify irregularities in the heart rhythm of the subject. Arrhythmias can be identified, for example, using the following procedure. Local maxima and minima are extracted from the signal in segments of the signal whose length is less than the typical RR interval. For example, 0.3 seconds is an appropriate segment length for this purpose. The width of each beat is defined, for example by measuring the time difference between successive locations of the signal values whose energy is equal to the average (e.g., a weighted average) of the local maximum and minimum. Beats with short width typically correspond to irregularities in the heart rhythm.

Detection of periodic limb movements can be detected, for example, by analyzing the amplitude of the signal and detecting variations at the maximum value. A thresholding procedure can then be employed for determining whether or not the amplitude changes at a rate which is sufficiently fast. The method can determine that periodic limb movements is detected when the amplitude changes at a rate which is above a predetermined threshold.

Procedures for detecting and identifying physiological events are disclosed in International Patent Publication Nos. WO2006/082589, WO2009/118737, U.S. Published Application Nos. 20070213620, 20070213621, 20070213622, 20070213624, 20080269583, 20060195037, U.S. Pat. No. 6,932,774, and U.S. Patent Application No. 61/254,704 the contents of which are hereby incorporated by reference).

From 12 the method optionally continues to decision 13. If a physiological event or noise is not detected for segment t, the method optionally proceeds to 14 at which the method calculates a transfer function filter, which represents the transfer function between the excitations pulses and atrial oxygenation signal. The transfer function filter can be estimated assuming that there are relatively slow or no variations of the heart rate and respiration rate and that its coefficients are constant with time.

If, on the other hand, a physiological event or noise is detected for segment t, the method optionally proceeds to 14 at which the segment is filtered using a transfer function filter. The filter employed at 14 can be a predetermined filter or a filter calculated for a segment t' which precedes segment t and for which no event was detected. From 15 the method optionally loops back to 11, wherein the features are extracted from the filtered segment. Thus, in this optional embodiment, following a detection of an abnormal event, the feature space is updated.

At 16 a path selection procedure is applied to the feature space $o_f$ for determining at least one sequence of respiration frequencies. The path selection procedure can feature any type of model or technique suitable for selecting a path within a multidimensional space. Representative examples of such models and techniques include, without limitation, hidden Markov model (HMM), dynamic programming, neural network, fuzzy logic, template matching and the like.

For a given sequence of feature spaces $O=(o_1, o_2, \ldots, o_T)$, where T is the number of segments of the signal, the path selection procedure selects a sequence of states $q=(q_1, q_2, \ldots q_T)$, where each state q corresponds to a respiration frequency or a range of respiration frequencies. Thus, the path selection procedure assigns a respiration frequency or a range of respiration frequencies for each segment of the signal.

Following is a description of a preferred path selection procedure which is based on a HMM. While the embodiments below are described with a particular emphasis to HMM, it is to be understood that more detailed reference to HMM is not to be interpreted as limiting the scope of the invention to HMM.

Figure 3:
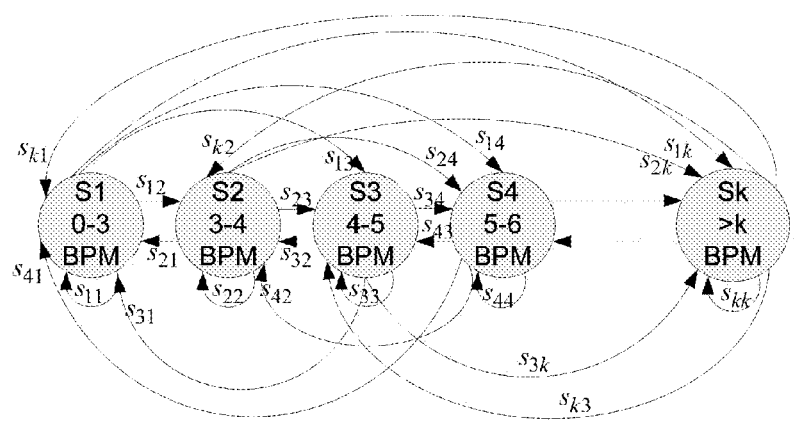

FIG. 3 is a schematic illustration of a discrete ergodic HMM. The model comprises k states, denoted, $s_1, s_2, \ldots, s_k$. A typical value for k is 40. Each of the k states of the model represents a possible respiration frequency. In the example illustrated in FIG. 2, the state $s_1$ corresponds to a frequency of 0-3 beats per minutes (BPM) of respiration, and states $s_2, \ldots, s_{k-1}$ respectively correspond to frequencies of 3-4, 4-5 ... (k–2)–(k–1) BPM. The kth state ($s_k$) is conveniently selected to represent all frequencies above k BPM. The state at time t is denoted $q_t$.

The procedure preferably calculates a transition probability from $q_t$ to $q_{t+1}$, which probability is denoted $s_{ij}(1 \le j \le k)$ with $i=q_t$ and $j=q_{t+1}$. Preferably, the procedure calculates the transition probability for a given status, where the status indicates whether or not a physiological event was detected for the t-th segment. In these embodiments, the probability is denoted $s_{ij}^l$, where the superscript l represents the status of the segment. Optionally, l also indicates the type of physiological event (that is, if the event was identified at 12). Thus, for example, l can receive four possible values, "AFIB", "PLMs", "apnea" and "Normal". Alternatively, l can be a binary index (e.g., TRUE when an event is detected and FALSE when an event is not detected).

The calculation of transition probability is preferably by means of a transition probability array. The transition probability array preferably is a three-dimensional array A whose elements are $s_{ij}^l$. A projection of such three-dimensional array for a given status l, can be written as the following matrix:

$$A_l = \begin{pmatrix} s_{11}^l & s_{12}^l & \ldots & s_{1k}^l \\ s_{21}^l & s_{22}^l & \ldots & s_{2k}^l \\ \vdots & \vdots & \ddots & \vdots \\ s_{k1}^l & s_{k2}^l & \ldots & s_{kk}^l \end{pmatrix}. \quad (2)$$

The array A can be estimated from a training data set. Generally, the values of the matrix $A_l$ are high near its diagonal, meaning that for a given status l, transitions between close states are more likely to occur.

For each of the k states, the procedure preferably calculates a probability distribution, $\xi_j$ which defines the distribution in the jth state, and optionally the l-th status. In some embodiments of the present invention $\xi$ is calculated using the following formula:

$$\xi_j^l(o_t) = P[o_t \mid q_t j, \text{status} = l] = \frac{1}{V} \sum_{v=1}^{V} G(o_t(v), \mu_j^l, \sigma_j^l), \, o_t \in \Re^V \quad (3)$$

where V is the number of the candidate frequencies in segment t, and G is a Gaussian probability density function centered at $\mu_j^l$ and having a width $\sigma_j^l$. Probability distributions functions, other that a Gaussian, are also contemplated. In some embodiments of the present invention the width $\sigma_j^l$ is calculated such that 95% of the Gaussian is within the relevant frequency.

For example, for state 2, which in the above example is defined for frequencies of 3-4 BPM, the center $\mu_2$ is 3.5 BPM and the width $\sigma_2$ is 0.25 BPM. In some embodiments of the present invention $\xi$ is estimated using expectation maximization algorithm for each of the status in the training set.

The initial state distribution is $\pi=\{\pi_i\}$, which in some embodiments is selected to be:

$$\pi_i = P[q_1 = i] = \frac{1}{k}. \quad (4)$$

In this embodiment, it is assumes that, initially, all states occur with the same probability. Other initial distributions can also be employed. For example, the process can be iterative, in which case the state distribution obtained after m−1 iterations is used as the initial the state distribution of the mth iteration.

As stated the procedure selects a sequence of states states $q=(q_1, q_2, \ldots, q_T)$, for a given sequence of observed feature spaces $O=(o_1, o_2, \ldots, o_T)$. It is convenient to define the following metric:

$$J_t(i, l) = \max_{q_1, q_2, \ldots, q_t} P[q_1 q_2 \ldots q_{t-1} q_t = i, \quad (5)$$
$$\text{status} = l, o_1, o_2, \ldots, o_t]$$

As can be understood from equation 5, $J_t(i,l)$ is the best score (highest probability) along single path at time t, which accounts for the first t feature spaces and ends at state i. $J_t(i,l)$ is preferably determined using the Viterbi algorithm.

Stated concisely, the Viterbi algorithm is in efficient method for selecting the path with maximal likelihood. The Viterbi algorithm is efficient because it does not compare all possible paths to the observed sequence. Instead, a shortest path algorithm is employed and paths that are far from being optimal are eliminated. The following procedure is preferably employed for each status l. For clarity of presentation, the status argument l is, therefore, omitted.

By induction:

$$J_{t+1}(i) = \left[\max_i J_t s_{ij}^l\right] \cdot \xi_j(o_{t+1}) \quad (6)$$

The argument that maximized the matrix $A_l$, for each t and j is determined using an array $\lambda_t(j)$, according to the following procedure:

A. Initialization:

$$J_1(i) = \pi_i \xi_i(o_1) = \xi_i(o_1)/k, \, 1 \leq i \leq N \quad (7)$$

$$\lambda_1(i) = 0 \quad (8)$$

B. Recursion:

$$J_t(j) = \max_{1 \leq i \leq N} (J_{t-1}(i) s_{ij}^l) \xi_i(o_t), \, 2 \leq t \leq T, \, 1 \leq i \leq N \quad (9)$$

$$\lambda_t(j) = \arg\max_{1 \leq i \leq N} (J_{t-1}(i) s_{ij}^l), \, 2 \leq t \leq T, \, 1 \leq i \leq N \quad (10)$$

C. Termination:

$$P^* = \max_{1 \leq i \leq N} (J_T(i)) \quad (11)$$

$$q_T^* = \arg\max_{1 \leq i \leq N} (J_T(i)) \quad (12)$$

D. The State Sequence:

$$q_t^* = \lambda_{t+1}(q_{t+1}^*), \, t=T-1, T-2, \ldots, 1. \quad (13)$$

Thus, the procedure selects a sequence of state estimates $\{q_t^*\}_{t=1}^T = (q_1^*, q_2^*, \ldots, q_T^*)$, hence also a sequence of respective respiration frequencies $\{f_t\}_{t=1}^T = (f_1, f_2, \ldots, f_T)$ or ranges of respiration frequencies. Optionally and preferably the method also selects 17 a corresponding sequence of respiration tidal volumes $b_t$, $1 \leq t \leq T$. This can be done using the following procedure, which is described for a given segment t.

The candidate frequencies in $F_t$ which are sufficiently close to $f_t$ are identified. For example, the method can select all the candidate frequencies in $F_t$ which are less than X Hz from $f_t$, where X is a predetermine frequency threshold, e.g., X=0.01. Assuming that there are z such candidate frequencies in $F_t$, the vector of indices of these frequencies is denoted $i_t$. Formally, $i_t = \arg(\text{abs}(F_t - f_t) < X)$. The respiration tidal volume $b_t$ can be calculated by averaging the components in $E_t$ that correspond to the indices in $i_t$. Formally: $b_t=\text{mean}(E_t(i_t))$.

At 18 the respiratory signal is reconstructed. In various exemplary embodiments of the invention the signal is reconstructed under the assumption that the respiration signal is a pure sinusoid. In some embodiments, the respiration signal is normalized using the tidal volumes $b_t$, as follows.

$$r[n]=b_t \cos(2\pi f_t+\phi_n), n=N_{sf}(t-1)+1, \ldots, N_{sf}t \quad (14)$$

where $N_{sf}$ is as defined hereinabove.

The reconstructed signal r[n] can be used as a discrete signal, wherein the argument t receives discrete values corresponding to the duration of the respective segments. Alternatively, the signal can be interpolated and be provided as a continuous signal.

The phase $\phi_t$ is initially zero and it is readily obtained from the last segment as $$\phi_t=\text{arc}\cos(\cos(2\pi f_{t-1}T+\phi_{t-1})). \quad (15)$$

Alternatively, the respiratory signal can be reconstructed under a different assumption, e.g., using an oscillatory function other than a pure sinusoid.

At 19 the method outputs the reconstructed signal, e.g., by transmitting it to a computer readable medium, from which the signal can be read and optionally displayed. The reconstructed signal can also be stored in the computer readable medium for subsequent use. For example, the respiratory signal can be telemetered out to the external programmer for display and analysis. Based on the information provided by the reconstructed signal, administered or other therapies can be adjusted appropriately The method ends at 20.

Figure 4:
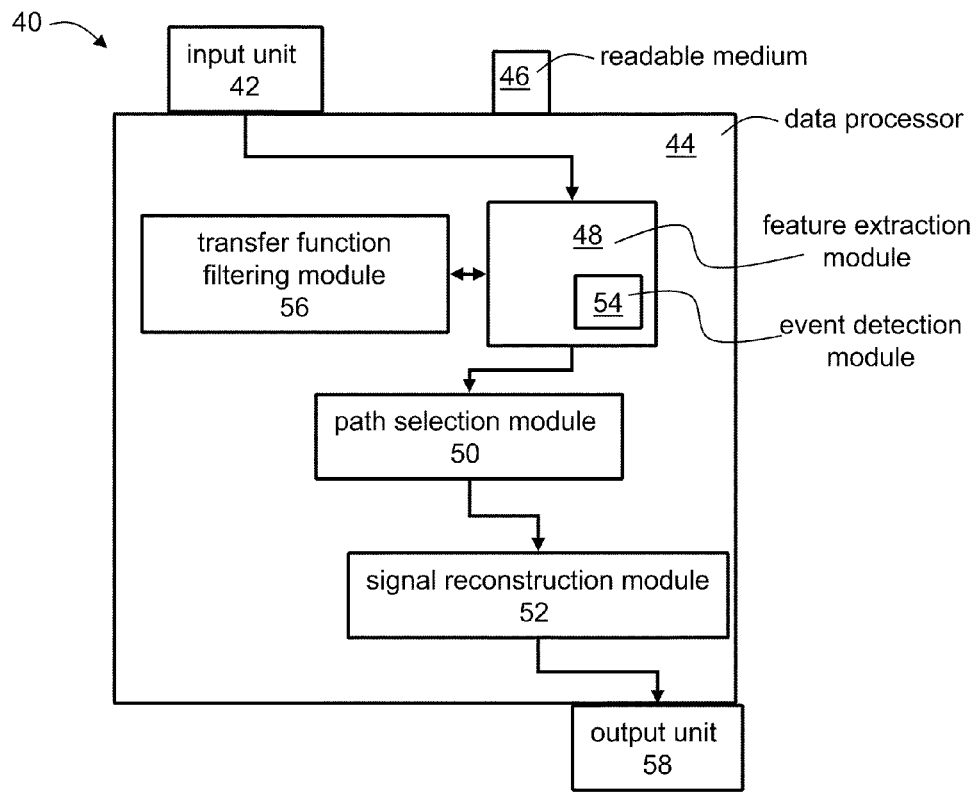

Reference is now made to FIG. 4 which is a schematic illustration of an apparatus 40 for analyzing a plethysmograph signal, according to various exemplary embodiments of the present invention. Apparatus 40 comprises an input unit 42 which receives the plethysmograph signal from a plethysmograph sensor or device (not shown, see FIG. 5), and a data processor 44.

Processor 44 can be supplemented with software which is embodied on a computer readable medium 46 accessible by processor 44. When the software is read by processor 44, the software cause processor to execute selected operations of the method described above. Processor 44 can also be a special computer having a feature extraction module 48, a path selection module 50, and a signal reconstruction module 52.

Feature extraction module 48 preferably extracts from the signal a plurality of features selected from the group consisting of respiration parameters, spectral parameters and signal envelope parameters, thereby constructing a feature space, as further detailed hereinabove. In some embodiments, module 48 comprises or is associated with an event detection module 54 which analyzes the signal, particularly the spectral parameters, for detecting temporal segments corresponding to a physiological event, as further detailed hereinabove. Feature extraction module 48 optionally receives physiological event data from event detection module 54, and updates the feature space following identification of segment corresponding to a physiological event, as further detailed hereinabove.

In various exemplary embodiments of the invention processor 44 also comprises a transfer function filtering module 56 which calculates a transfer function filter h for each segment other than segments corresponding to physiological events. Module 56 applies the calculated filter h to subsequent temporal segments for which a physiological event was identified. The thus filtered segments are returned to feature extraction module 48 which perform the extraction operation using the filtered segment.

Path selection module 50 employs a path selection procedure to the feature space for determining at least one sequence of respiration frequencies $(f_1, f_2, \ldots, f_T)$, as further detailed hereinabove. In various exemplary embodiments of the invention module 50 employs a procedure featuring a HMM. Module 50 can also be designed and constructed to employ the expectation maximization algorithm and/or Viterbi algorithm. Other type of path selection procedures are not excluded from the scope of the present invention. Module 50 preferably receives physiological events data from module 54 and employs the path selection procedure separately for different types of physiological events.

Signal reconstruction module 52 receives the sequence of respiration frequencies and reconstructs a respiratory signal using the sequence, as further detailed hereinabove. In various exemplary embodiments of the invention module 52 reconstruct the signal as a pure sinusoidal signal. Module 52 optionally and preferably interpolates the sequence of respiration frequencies so as to provide a continuous respiratory signal. In various exemplary embodiments of the invention module 52 also determine respiration tidal volumes, as further detailed hereinabove. Module 52 can output the information (respiratory signal and optionally respiration tidal volumes) through an output unit 58.

Figure 5:
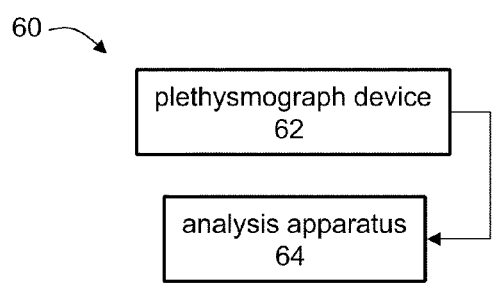

Reference is now made to FIG. 5 which is a schematic illustration of a plethysmograph system 60, according to various exemplary embodiments of the present invention. System 60 comprises a plethysmograph sensor or device 62 which generates a plethysmograph signal. In some embodiments of the present invention plethysmograph device 62 is a photoplethysmograph device. System 60 further comprises an analysis apparatus 64 which analyzes the plethysmograph signal and reconstructs a respiratory signal, as further detailed hereinabove. In various exemplary embodiments of the invention apparatus 64 is the same as apparatus 40 described above.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of analyzing a photoplethysmograph signal, comprising:
   segmenting the photoplethysmograph signal into at least a plurality of temporal segments;
   extracting from each temporal segment of said plurality of temporal segments a plurality of features including at least respiration parameters, to construct a multidimensional feature space;
   employing a path selection procedure to said multidimensional feature space to assign a respiration frequency or a range of respiration frequencies separately for each segment of said plurality of temporal segments, thereby determining at least one sequence of respiration frequencies, wherein each respiration frequency or range of respiration frequencies corresponds to a state of said multidimensional feature space and wherein said path selection procedure calculates probabilities of transitions between states;
   reconstructing a respiratory signal using said sequence; and
   displaying said reconstructed respiratory signal and adjusting a therapy based on said displayed reconstructed respiratory signal.

2. The method according to claim 1, further comprising using said sequence of respiration frequencies for selecting a corresponding sequence of respiration tidal volumes.

3. The method according to claim 1, wherein said plurality of features further comprises spectral parameters, and the method further comprises analyzing the spectral parameters for detecting temporal segments corresponding to a physiological event, wherein said path selection procedure is employed separately for different types of physiological events.

4. The method according to claim 3, wherein said physiological event is selected from the group consisting of atrial fibrillation, periodic limb movements and apnea.

5. The method according to claim 3, further comprising updating said feature space following identification of a segment corresponding to a physiological event.

6. The method according to claim 5, further comprising calculating a transfer function filter for each segment other than segments corresponding to physiological events, wherein said updating of said feature space comprises filtering a respective segment corresponding to a respective physiological event using a transfer function filter of a preceding segment.

7. The method according to claim 1, wherein said path selection procedure comprises an expectation maximization algorithm.

8. The method according to claim 1, wherein said path selection procedure features a hidden Markov model.

9. Apparatus for analyzing a photoplethysmograph signal, comprising:
   an input unit for receiving the photoplethysmograph signal; and
   a data processor configured for segmenting the photoplethysmograph signal into at least a plurality of temporal segments; extract from each temporal segment of said plurality of temporal segments a plurality of features including at least respiration parameter, thereby constructing a multidimensional feature space; employing a path selection procedure to said multidimensional feature space to assign a respiration frequency or a range of respiration frequencies separately for each segment of said plurality of temporal segments, thereby determining at least one sequence of respiration frequencies; reconstructing a respiratory signal using said sequence, wherein each respiration frequency or range of respiration frequencies corresponds to a state of said feature space and wherein said path selection procedure calculates probabilities of transition between states, and displaying said reconstructed respiratory signal.

10. The apparatus according to claim 9, wherein said data processor is configured for using said sequence of respiration frequencies for selecting a corresponding sequence of respiration tidal volumes.

11. The apparatus according to claim 9, wherein said plurality of features further comprises spectral parameters, and wherein said data processor is configured for analyzing the spectral parameters for temporal segments corresponding to a physiological event, wherein said path selection procedure is employed separately for different types of physiological events.

12. The apparatus according to claim 11, wherein said physiological event is selected from the group consisting of atrial fibrillation, periodic limb movements and apnea.

13. The apparatus according to claim 11, wherein said data processor is configured for updating said feature space following identification of segment corresponding to a physiological event.

14. The apparatus according to claim 13, wherein said data processor is configured for calculating a transfer function filter for each segment other than segments corresponding to physiological events, wherein said updating of said feature space comprises filtering a respective segment corresponding to a respective physiological event using a transfer function filter of a preceding segment.

15. The apparatus according to claim 9, wherein said path selection procedure comprises an expectation maximization algorithm.

16. The apparatus according to claim 9, wherein said path selection procedure features a hidden Markov model.

17. A photoplethysmograph system, comprising;
a photoplethysmograph sensor configured for generating a photoplethysmograph signal and an analysis apparatus which comprises an input unit for receiving the photoplethysmograph signal; and
a data processor configured for segmenting the photoplethysmograph signal into at least a plurality of temporal segments; extracting from each temporal segment of said plurality of temporal segments a plurality of features including at least respiration parameters, thereby constructing a multidimensional feature space; employing a path selection procedures to said multidimensional feature space to assign a respiration frequency or a range of respiration frequencies separately for each segment of said plurality of temporal segments, determining at least one sequence of respiration frequencies; reconstructing a respiratory signal using said sequence, wherein each respiration frequency or range of respiration frequencies corresponds to a state of said feature space and wherein said path selection procedure calculates probabilities of transitions between states, and displaying said reconstructed respiratory signal.

18. A method of assessing respiration of a subject, comprising connecting a photoplethysmograph sensor to the subject and analyzing a photoplethysmograph signal received from said sensor using the method of claim 1.

19. The method of claim 1, wherein said plurality of features comprises at least one additional feature selected from the group consisting of spectral parameters and signal envelope parameters.

20. The apparatus of claim 9, wherein said plurality of features comprises at least one additional feature selected from the group consisting of spectral parameters and signal envelope parameters.

* * * * *